Figure 1:
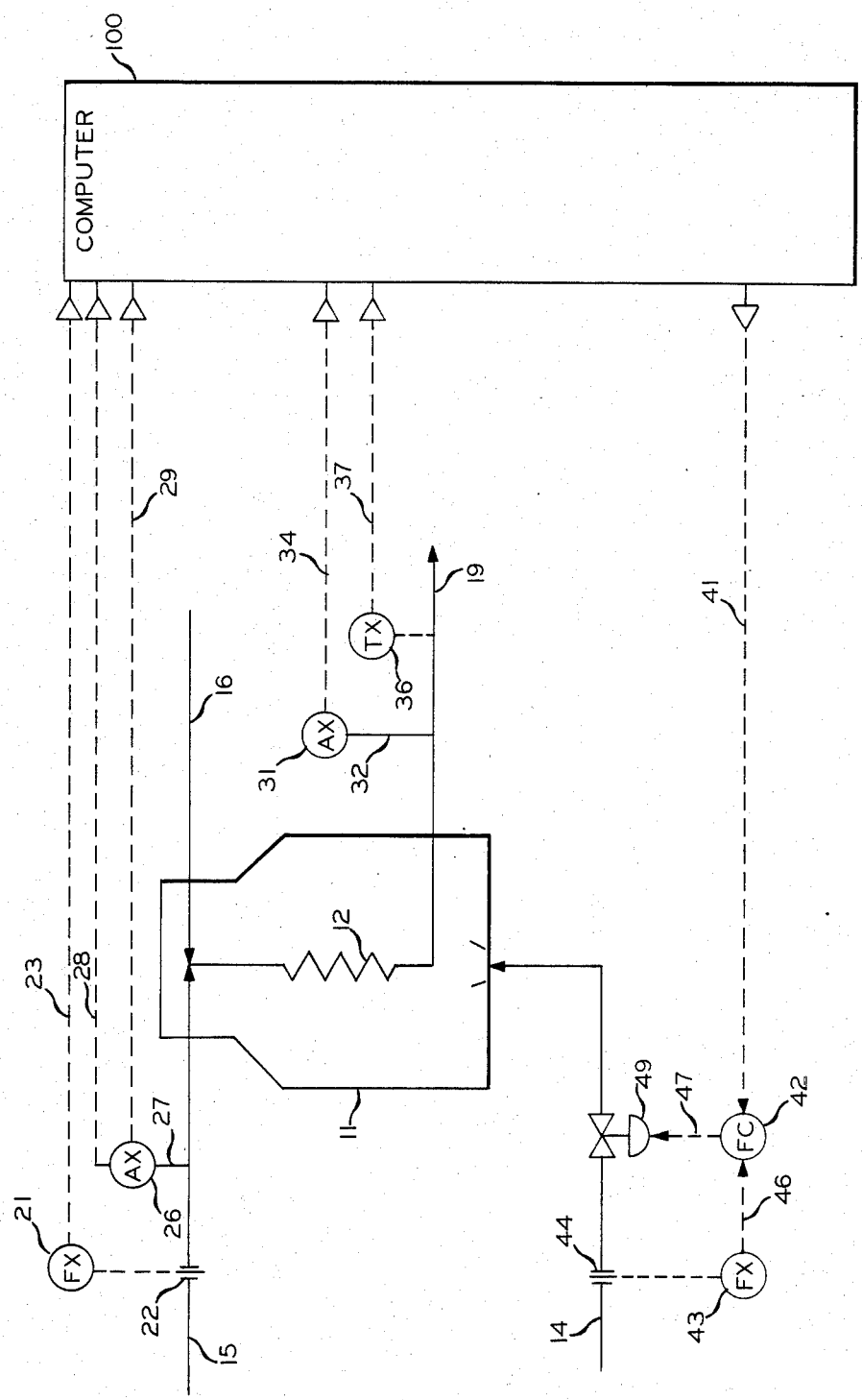

United States Patent [19]

Hobbs

[11] Patent Number: 4,536,606

[45] Date of Patent: Aug. 20, 1985

[54] CONTROL OF A CRACKING FURNACE

[75] Inventor: James W. Hobbs, Sweeny, Tex.

[73] Assignee: Phillips Petroleum Company, Bartlesville, Okla.

[21] Appl. No.: 242,491

[22] Filed: Mar. 10, 1981

[51] Int. Cl.³ .................. C07C 4/02; G01N 31/00; G06F 7/58
[52] U.S. Cl. .................................... 585/650; 364/500
[58] Field of Search .................. 23/230 A; 364/500; 585/650

[56] References Cited

U.S. PATENT DOCUMENTS

| | | | |
|---|---|---|---|
| 2,618,668 | 11/1952 | O'Connor et al. | 585/650 X |
| 2,860,174 | 11/1958 | Begley et al. | 585/650 X |
| 3,271,472 | 9/1966 | Ogle et al. | 585/501 |
| 3,824,388 | 7/1974 | Cugini | 585/650 X |
| 4,231,753 | 11/1980 | Stewart | 23/230 A |
| 4,236,218 | 11/1980 | Kilbrew, Jr. | 364/500 |

Primary Examiner—Robert V. Hines
Attorney, Agent, or Firm—French & Doescher

[57] ABSTRACT

The heat provided to a cracking furnace is manipulated so as to maintain the actual conversion of a first component in the feed stream flowing to the cracking furnace substantially equal to the desired conversion for the first component. The actual conversion of the first component is determined based on an analysis for the concentration of the first component in the feed stream flowing to the cracking furnace, an analysis of the concentration of the first component in the product stream flowing from the cracking furnace, an estimate of the conversion of the first component and a calculation of the expansion of the feed stream in the cracking furnace. The thus derived actual conversion is compared to a desired conversion with the results of the comparison being utilized in combination with the feed flow rate to manipulate the heat provided to the cracking furnace.

11 Claims, 2 Drawing Figures

CONTROL OF A CRACKING FURNACE

This invention relates to control of a cracking furnace. In one aspect this invention relates to method and apparatus for determining the percent conversion of a component in the feed stream flowing to the cracking furnace. In another aspect this invention relates to method and apparatus for controlling a cracking furnace so as to maintain a desired percent conversion.

The cracking furnace forms the heart of many chemical manufacturing processes. Often the performance of the cracking furnace will carry the burden of the major profit potential for the entire manufacturing process. Close control of the cracking furnace is required to maximize the profitability of the chemical manufacturing process.

In a manufacturing process such as the manufacture of ethylene, a suitable feed stream such as a mixture of ethane and propane is fed into the cracking furnace. Within the furnace, at least a portion of the ethane and propane are cracked. If the feed gas is a mixture of ethane and propane, the gaseous mixture removed from the cracking furnace will primarily contain hydrogen, methane, ethylene, ethane, propylene and propane.

After removal from the cracking furnace, the gaseous mixture is cooled and compressed. The thus compressed mixture is generally routed through various distillation columns where individual components such as ethylene are purified and separated. The separated products, of which ethylene is the major product, then leave the ethylene plant to be used in numerous other processes for the manufacture of a wide variety of secondary products.

A number of performance parameters may be utilized to evaluate the performance of a cracking furnace or control a cracking furnace. One such operating parameter is conversion. As used herein, the term "conversion" refers to the number of mols of a component in the feed which are cracked in one pass through the cracking furnace. For an ethane-propane mix, conversion could refer to the number of mols of feed ethane which are cracked in one pass through the cracking furnace.

Virtually 100 percent conversion of ethane may be obtained if high temperatures and long residence times are used. However, high percent conversion may result in poor selectivity of the cracking of ethane to ethylene. Unwanted byproducts such as methane and acetylene are formed at high conversion rates and also coke is produced more rapidly at high conversion rates.

In contrast, if the conversion of ethane is low, the overall production of ethylene will be impaired and also substantially larger expenditures of energy will be required by the cracking process to produce a given volume of ethylene. Thus, it is desirable to maintain a conversion which provides an acceptable selectivity, ethylene production and energy use.

It is thus an object of this invention to provide method and apparatus for maintaining a desired conversion of a component, such as ethane, in the feed stream flowing to a cracking furnace.

In the past, analysis of all components in the furnace effluent has been required to calculate conversion of a component such as ethane. However, since a commercial cracking furnace may have a number of effluent streams, it is very costly to perform a full component analysis on each of the effluent streams and it is difficult to maintain the analyzers to provide such an analysis quickly. Also, a full component analysis may take a substantial length of time even if only one effluent stream is used and thus process control is impaired because up-to-date information is not available on conversion. It is thus an object of this invention to provide an improved method and apparatus for determining conversion of a component in the feed stream flowing to a cracking furnace.

In accordance with the present invention, method and apparatus is provided whereby conversion of a first component in the feed stream flowing to a cracking furnace is determined based on an analysis of the concentration of at least the first component in the feed stream and based on an analysis of the concentration of the first component in all furnace effluent streams. In general, the conversion may be determined based on the aforementioned analysis by estimating the conversion of the first component based on previous experience with the cracking furnace. The conversion of other components, if any, were analyzed for in the feed stream is then determined. The molecular expansion due to cracking of the first component and any other components which were analyzed for in the feed stream is then determined and the actual analysis and expansions are utilized to calculate an overall expansion. An actual conversion of the first component is then determined based on the overall expansion and the analysis of the first component in the feed stream and in the effluent streams. A new estimated ethane conversion is then determined based on the computed ethane conversion. Repetition of the above steps the desired number of times may be used to provide an extremely accurate actual first component conversion.

The thus determined actual first component conversion is then utilized to control the cracking furnace so as to maintain the actual first component conversion substantially equal to a desired first component conversion. In general this may be accomplished by comparing the actual first component conversion to a desired first component conversion to derive a furnace outlet temperature required to maintain the actual first component conversion substantially equal to the desired first component conversion. The actual furnace outlet temperature is then compared to the required furnace outlet temperature to derive a control signal which is utilized to manipulate the flow of fuel to the furnace so as to maintain the actual furnace outlet temperature substantially equal to the required furnace outlet temperature.

Figure 2:
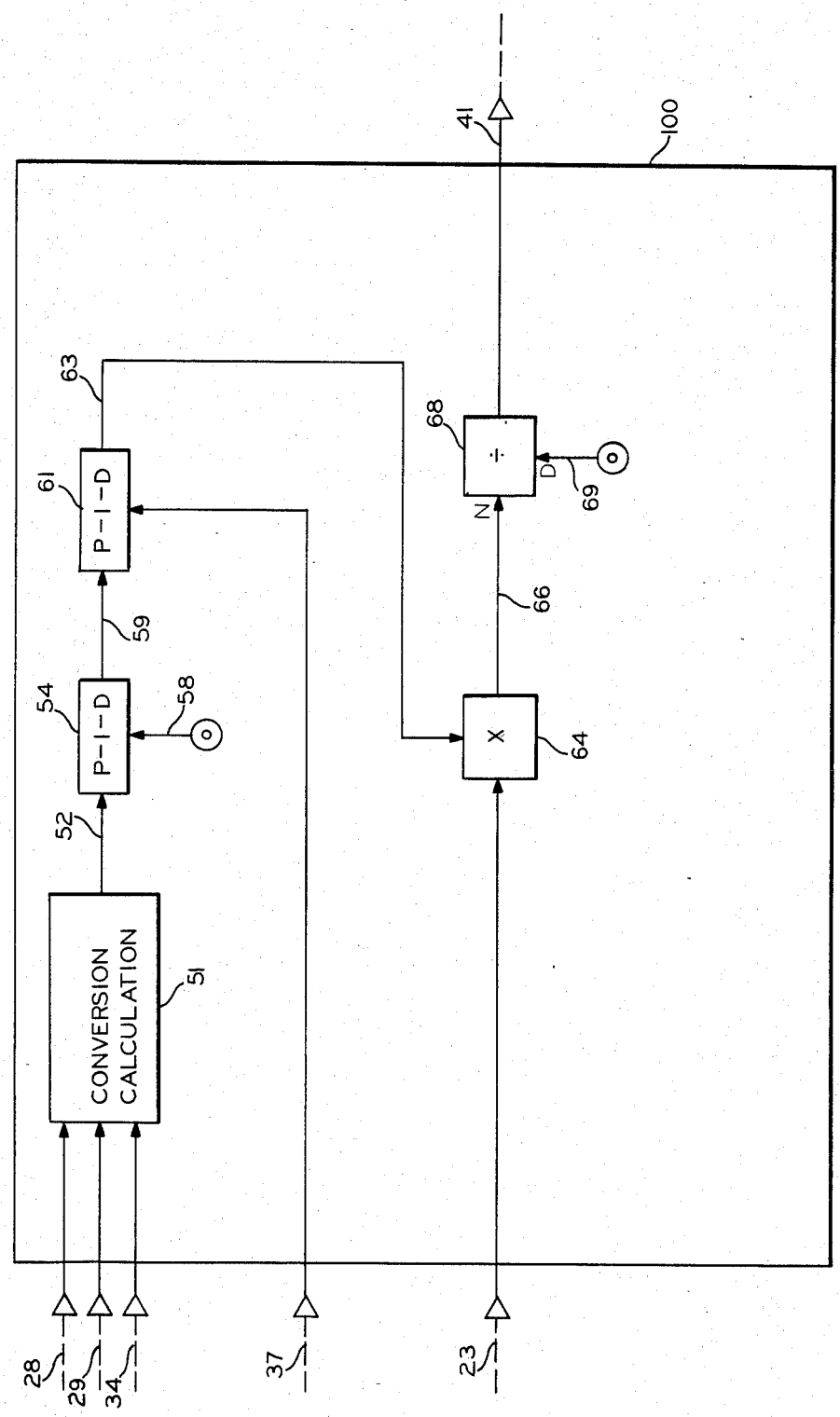

Other objects and advantages of the invention will be apparent from the foregoing brief description of the invention and the claims as well as from the drawings in which:

FIG. 1 is a diagrammatic illustration of a cracking furnace together with the control system of the present invention for the cracking furnace; and FIG. 2 is a logic diagram of the computer logic utilized to generate the control signals illustrated in FIG. 1 based on the process measurements.

For the sake of simplicity, the invention is illustrated and described in terms of a single cracking furnace. However, the invention is also applicable to multiple furnaces.

The invention is also illustrated and described in terms of a process for the manufacture of ethylene. However, the applicability of the invention described herein extends to other processes wherein a cracking furnace is utilized to crack a feed into some desired components. The feed stream utilized is a mixture of ethane and propane with ethane being the predominant component. Also the conversion of ethane is utilized to control the cracking furnace. However, the applicability of the invention extends to the use of other feed streams such as a pure ethane or a naphtha feed stream and also conversion of a component other than ethane may be determined and utilized to control the cracking furnace.

Only the parts of the cracking furnace and the control elements for the cracking furnace required to illustrate the present invention are illustrated in FIG. 1 for the sake of simplicity. Process control equipment other than that illustrated in FIG. 1 would be utilized to control a cracking furnace. As an example, the flow of steam to the cracking furnace would generally be manipulated so as to maintain a desired ratio of the steam flow rate to the feed flow rate. Also, additional equipment such as heat exchangers and pumps would be utilized. However, the additional equipment required is well known and has been utilized for many years with cracking furnaces.

A specific control system configuration is set forth in FIG. 1 for the sake of illustration. However, the invention extends to different types of control system configurations which accomplish the purpose of the invention. Lines designated as signal lines in the drawings are electrical or pneumatic in this preferred embodiment. Generally, the signals provided from any transducer are electrical in form. However, the signals provided from flow sensors will generally be pneumatic in form. Transducing of these signals is not illustrated for the sake of simplicity because it is well known in the art that if a flow is measured in pneumatic form it must be transduced to electrical form if it is to be transmitted in electrical form by a flow transducer. Also, transducing of the signals from analog form to digital form or from digital form to analog form is not illustrated because such transducing is also well known in the art.

The invention is also applicable to mechanical, hydraulic or other signal means for transmitting information. In almost all control systems some combination of electrical, pneumatic, mechanical or hydraulic signals will be used. However, use of any other type of signal transmission, compatible with the process and equipment in use, is within the scope of the invention.

A digital computer is used in the preferred embodiment of this invention to calculate the required control signals based on measured process parameters as well as set points supplied to the computer. Analog computers or other types of computing devices could also be used in the invention. The digital computer is preferably an OPTROL 7000 Process Computer System from Applied Automation, Inc., Bartlesville, Okla.

Signal lines are also utilized to represent the results of calculations carried out in a digital computer and the term "signal" is utilized to refer to such results. Thus, the term signal is used not only to refer to electrical currents or pneumatic pressures but is also used to refer to binary representations of a calculated or measured value.

Both the analog and digital controllers shown may utilize the various modes of control such as proportional, proportional-integral, proportional-derivative, or proportional-integral-derivative. In this preferred embodiment, proportional-integral-derivative controllers are utilized but any controller capable of accepting two input signals and producing a scaled output signal, representative of a comparison of the two input signals, is within the scope of the invention. The operation of proportional-integral-derivative controllers is well known in the art. The output control signal of a proportional-integral-derivative controller may be represented as $$S = K_1 E + K_2 \int E dt + K_3 (dE/dT)$$

where
S = output control signals;
E = difference between two input signals; and
$K_1$, $K_2$ and $K_3$ = constants.

The scaling of an output signal by a controller is well known in control system art. Essentially, the output of a controller may be scaled to represent any desired factor or variable. An example of this is where a desired flow rate and an actual flow rate is compared by a controller. The output could be a signal representative of a desired change in the flow rate of some gas necessary to make the desired and actual flows equal. On the other hand, the same output signal could be scaled to represent a percentage or could be scaled to represent a temperature change required to make the desired and actual flows equal. If the controller output can range from 0 to 10 volts, which is typical, then the output signal could be scaled so that an output signal having a voltage level of 5.0 volts corresponds to 50 percent, some specified flow rate, or some specified temperature.

The various transducing means used to measure parameters which characterize the process and the various signals generated thereby may take a variety of forms or formats. For example, the control elements of the system can be implemented using electrical analog, digital electronic, pneumatic, hydraulic, mechanical or other similar types of equipment or combinations of one or more such equipment types. While the presently preferred embodiment of the invention preferably utilizes a combination of pneumatic final control elements in conjunction with electrical analog signal handling and translation apparatus, the apparatus and method of the invention can be implemented using a variety of specific equipment available to and understood by those skilled in the process control art. Likewise, the format of the various signals can be modified substantially in order to accommodate signal format requirements of the particular installation, safety factors, the physical characteristics of the measuring or control instruments and other similar factors. For example, a raw flow measurement signal produced by a differential pressure orifice flow meter would ordinarily exhibit a generally proportional relationship to the square of the actual flow rate. Other measuring instruments might produce a signal which is proportinal to the measured parameter, and still other transducing means may produce a signal which bears a more complicated, but known, relationship to the measured parameter. Regardless of the signal format or the exact relationship of the signal to the parameter which it represents, each signal representative of a measured process parameter or representative of a desired process value will bear a relationship to the measured parameter or desired value which permits designation of a specific measured or desired value by a specific signal value. A signal which is representative of a process measurement or desired process value is therefore one from which the information regarding the measured or desired value can be readily retrieved regardless of the exact mathematical relationship between the signal units and the measured or desired process units.

Referring now to FIG. 1, a conventional cracking furnace 11 is illustrated having a cracking tube 12. Heat is supplied to the cracking tube 12 by a burner which is supplied with fuel through conduit means 14. Ordinarily, a cracking furnace used in a process such as the manufacture of ethylene will have a larger number of cracking tubes and a large number of burners. Also, in a process such as the manufacture of ethylene a plurality of cracking furnaces will commonly be utilized. A mixture of ethane and propane is provided as a feed to the cracking furnace 11 through conduit means 15. The feed flowing through conduit means 15 preferably contains a high concentration of ethane and pure ethane would generally be the preferred feed if such a feed were readily available. Feeds containing 90 percent ethane are commonly utilized.

Steam is provided to the cracking furnace 11 through conduit means 16. The feed stream flowing through conduit means 15 and the steam flowing through conduit means 16 are combined within the cracking furnace 11 and flow through the cracking tube 12. After passing through the cracking tube 12, in which the ethane is converted at least in part to ethylene and the propane is converted at least in part to propylene, the reaction effluent is withdrawn through conduit means 19 and is provided to the remainder of the ethylene process. Just as the typical cracking furnace will contain more than one cracking tube, the typical cracking furnace will also generally have a plurality of effluent streams for removing the reaction effluent from the plurality of cracking tubes.

Flow transducer 21 in combination with the flow sensor 22, which is operably located in conduit means 15, provides an output signal 23 which is representative of the flow rate of the feed flowing through conduit 15. Signal 23 is provided from the flow transducer 21 as an input to computer means 100.

The analyzer transducer 26 is preferably a chromatographic analyzer. A sample of the feed flowing through conduit means 15 is provided to the analyzer transducer 26 through conduit means 27. For the mixture of ethane and propane of the example feed stream, the analyzer transducer 26 provides the mol fraction of ethane in the feed stream flowing through conduit means 15 and the mol fraction of propane in the feed stream flowing through conduit means 15. Signal 28, which is representative of the mol fraction of ethane in the feed flowing through conduit means 15 and signal 29 which is representative of the mol fraction of propane in the feed flowing through conduit means 15 are both provided as inputs to computer means 100.

Analyzer transducer 31 is also preferably a chromatographic analyzer. The same chromatographic analyzer can be used for analyzer transducer 26 and analyzer transducer 31 if a sample of the fluid flowing through conduit means 15 and the fluid flowing through conduit means 19 can be provided to a single analyzer. A sampe of the effluent flowing through conduit means 19 is provided to the analyzer transducer 31 through conduit means 32. The analyzer transducer 31 provides an output signal 34 which is representative of the mol fraction of ethane in the effluent flowing through conduit means 19. It is noted that only the single analysis for the effluent stream (in this case an analysis of ethane since ethane conversion is being utilized as an example) is required to determine ethane conversion in accordance with the present invention. Signal 34 is provided from the analyzer transducer 31 as an input to computer means 100.

Temperature transducer 36 in combination with a temperature sensing device such as a thermocouple, which is operably located in conduit means 19, provides an output signal 37 which is representative of the temperature of the effluent flowing through conduit means 19. This temperature is typically referred to as the "coil outlet temperature" and will generally be representative of the outlet temperature of the cracking tube 12. Signal 37 is provided from the temperature transducer 36 as an input to computer means 100.

In response to the described input signals, computer means 100 calculates the flow rate of the fuel flowing through conduit means 14 required to maintain the actual ethane conversion substantially equal to the desired ethane conversion. Signal 41, which is representative of the required fuel flow rate, is provided from computer means 100 as a set point to the flow controller 42. The flow transducer 43 in combination with the flow sensor 44, which is operably located in conduit means 14, provides an output signal 46 which is representative of the actual flow rate of the fuel flowing through conduit means 14. Signal 46 is provided as the process variable input to the flow controller 42. The flow controller 42 provides an output signal 47 which is responsive to the difference between signals 41 and 46. Signal 47 is provided by a control signal to the control valve 49 which is operably located in conduit means 14. The control valve 49 is manipulated in response to signal 47 to thereby maintain the actual flow rate of the fuel flowing through conduit means 14 substantially equal to the desired flow rate of the fuel flowing through conduit means 14 as represented by signal 41.

The following discussion regarding the calculation of the actual ethane conversion for the present invention is provided to simplify the computer logic illustrated in FIG. 2 and illustrate the basis for the conversion calculation. All equations are written in a form which is suitable for use in a computer program.

An operator for a cracking furnace will generally have a feeling for the percent ethane conversion. The first step in determining the actul ethane conversion is to establish such an estimated ethane conversion. The propane conversion may be derived from a plot of simultaneous conversion for light hydrocarbons such as is illustrated in Schutt, H. C., *Chemical Engineering Progress,* Volume 43, page 103, March, 1947. Use of such a plot provides:

$$Y3 = 1. - (1. - Y2)^{**}2.8885 \qquad (1)$$

where $Y3$ = propane conversion; and $Y2$ = estimated ethane conversion from the first step. In actuality the value of $Y3$ in Equation (1) will be an estimate the accuracy of which is directly related to the accuracey of the estimate of $Y2$.

The molecular expansion of ethane and propane in the cracking furnace may be determined from a plot of expansion versus conversion such as is illustrated in Zdonik, S. B., et al, "Manufacturing Ethylene", page 30, *Petroleum Publishing Company,* Tulsa, Okla., 1970. Use of such a plot provides:

$$A2 = 0.93657^{*}Y2 + 1.0042 \qquad (2)$$

$$A3 = 0.91075^{*}Y3 + 1.0034 \qquad (3)$$

where

A2=ethane expansion; and

A3=propane expansion.

The overall expansion in the cracking furnace is given by:

$$A = 1. - X2 - X3 + X2*A2 + X3*A3 \quad (4)$$

where

A=overall expansion.

A new ethane conversion which takes overall expansion into account may then be calculated utilizing:

$$Y2E = 1. - A*(Z2/X2) \quad (5)$$

where

Y2E=new ethane conversion;

Z2=mole fraction of ethane in the effluent; and

X2=mole fraction of ethane in the feed.

A new estimated ethane conversion can then be calculated using:

$$Y2 = Y2 + 0.5(Y2E - Y2). \quad (6)$$

In general, the Y2 provided by the results of Equation (6) will be 50 percent more accurate than the estimated Y2 which was initially chosen. If there is a high degree of confidence in the first estimated ethane conversion, the results of Equation (6) may be utilized as the actual ethane conversion. However, it is generally preferred to repeat the above steps four times with the results of Equation (6) being utilized as the estimated ethane conversion in Equations (1) and (3) each time. Use of Equations (1)-(6) with repetition four times has provided the following results on a commercial cracking furnace:

| ETHANE CONVERSION | |
|---|---|
| Actual | Determined In Accordance With Invention |
| 59.9% | 59.6% |
| 59.7% | 60.3% |
| 61.0% | 60.4% |

It can thus be seen that the ethane conversion can be determined in accordance with the present invention based on an analysis of only the ethane in the effluent and that a full component analysis for the effluent is not required.

It is noted that if the feed were pure ethane, then only an estimate of ethane conversion and Equations (2), (4), (5) and (6) would be used. The terms X3 and X3 * A3 would also be deleted from Equation (4). It is also noted that even if the feed is not pure ethane, the feed may be treated as pure ethane but the accuracy of the conversion calculation will be affected.

If the feed contains components other than ethane and propane that are cracked, it is preferred to take these components into consideration in calculating the overall expansion A. This may be accomplished in the same manner as previously described for propane. Also, the conversion of propane or another component cracked in the furnace may be calculated in the same manner as described for ethane.

The logic flow diagram utilized to calculate the control signal 41 in response to the previously described input signal to computer means 100 is illustrated in FIG. 2. Referring now to FIG. 2, computer means 100 is shown as a solid line surrounding the flow logic.

Signal 28 which is representative of the mol fraction of ethane in the feed is provided as an input to the conversion calculation block 51. In like manner, signal 29 which is representative of the mol fraction of propane in the feed and signal 34 which is representative of the mol fraction of ethane in the effluent are provided as inputs to the conversion calculation block 51. The actual conversion of ethane is calculated as has been previously described and signal 52 which is representative of such actual conversion of ethane is provided from the conversion calculation block 51 as the process variable input to the proportional-integral-derivative (P-I-D) block 54.

The P-I-D block 54 is also provided with a set point signal 58 which is representative of the desired ethane conversion. Signal 58 will generally be in the range of about 59% to about 63%. The P-I-D block 54 provides an output signal 59 which is responsive to the difference between signals 52 and 58. Signal 59 is scaled so as to be representative of the temperature of the effluent required to maintain the actual ethane conversion substantially equal to the desired ethane conversion. Signal 59 is provided from the P-I-D controller block 54 as a set point to the P-I-D controller block 61.

The P-I-D controller block 61 is also provided with signal 37 which is representative of the actual effluent temperature. Signal 37 is provided as the process variable input to the P-I-D controller block 61. The P-I-D controller block 61 provides an output signal 63 which is responsive to the difference between signals 59 and 37. Signal 63 is scaled so as to be representative of the number of BTU's which must be provided per pound of feed to maintain the actual effluent temperature substantially equal to the required effluent temperature as represented by signal 59. Signal 63 is provided from the P-I-D controller block 61 as an input to the multiplying block 64.

The multiplying block 64 is also provided with signal 63 which is representative of the feed flow rate. Signal 23 is multiplied by signal 63 to provide signal 66 which is representative of the number of BTU's which must be provided to the cracking furnace per unit time. Use of the feed flow rate to determine the number of BTU's which must be provided to the cracking furnace per unit time provides the advantage of compensating for changes in the feed flow rate and thus provides feed-forward control for the cracking furnace. Signal 66 is provided from the multiplying block 64 to the numerator input of the dividing block 68.

Signal 69, which is representative of the number of BTU's contained in each standard cubic foot of the fuel flowing through conduit means 14, is provided to the denominator of the input of the dividing block 68. It is noted, that if the BTU content of the fuel flowing through conduit means 14 varies widely, then analysis of the fuel to determine the BTU content will be required on a continuous basis with such analysis being utilized to provide signal 69. Signal 66 is divided by signal 69 to provide signal 41 which is representative of the number of standard cubic feet of fuel which must be provided per unit time to the cracking furnace 11. Signal 41 is utilized as has been previously described.

The invention has been described in terms of a preferred embodiment as illustrated in FIGS. 1 and 2. Specific components which can be used in the practice of the invention as illustrated in FIG. 1 such as flow sensors 22 and 44; flow transducers 21 and 43; temperature transducer 36; flow controller 42 and control valve 49 are each well known, commercially available control components such as are illustrated and described at length in Perry's *Chemical Engineer's Handbook*, 4th Edition, Chapter 22, McGraw Hill. A suitable analyzer 26 and 31 is the Process Chromatograph System, Model 102, manufactured by Applied Automation, Inc., Bartlesville, Okla.

While the invention has been described in terms of the presently preferred embodiment, reasonable variations and modifications are possible by those skilled in the art, within the scope of the described invention and the appended claims.

That which is claimed is:

1. A method for controlling a cracking furnace in which a feed stream is cracked to produce a gaseous mixture which contains both components which were originally in said feed stream and components which are produced by the cracking of the original components in said feed stream, said method comprising the steps of:
   (a) analyzing said feed stream to determine the concentration (X2) of a first component in said feed stream;
   (b) analyzing said gaseous mixture to determine the concentration (Z2) of said first component in said gaseous mixture;
   (c) estimating the conversion (Y2) of said first component in said cracking furnace;
   (d) calculating the expansion (A2) of said first component in said cracking furnace based on the value of Y2 and expansion versus conversion data
   (e) calculating the expansion (A) of said feed stream in said cracking furnace based on the value of X2 and A2;
   (f) calculating the conversion (Y2E) of said first component based on the value of A, X2 and Z2;
   (g) calculating a new estimated conversion of said first component based on the value of Y2 and Y2E and establishing a first signal representative of the new estimated conversion;
   (h) establishing a second signal representative of the desired conversion of said first component;
   (i) comparing said first signal and said second signal and establishing a third signal which is responsive to the difference between said first signal and said second signal; and
   (j) manipulating the heat supplied to said cracking furnace in response to said third signal to thereby maintain said first signal substantially equal to said second signal.

2. A method in accordance with claim 1 wherein said first component is ethane and ethane is the primary component of said feed stream.

3. A method in accordance with claim 1 additionally comprising the step of repeating steps d-g at least four times, using the new estimated conversion derived in step g each time in step d, to establish said first signal.

4. A method in accordance with claim 1 wherein a fuel is supplied to said cracking furnace with the combustion of said fuel supplying heat to said cracking furnace, wherein said third signal is scaled so as to be representative of the temperature of said gaseous mixture required to maintain said first signal substantially equal to said second signal and wherein said step of manipulating the heat provided to said cracking furnace in response to said third signal comprises:

establishing a fourth signal which is representative of the actual temperature of said gaseous mixture;

comparing said third signal and said fourth signal and establishing a fifth signal which is responsive to the difference between said third signal and said fourth signal, wherein said fifth signal is scaled so as to be representative of the heat which must be provided to said cracking furnace per unit of said feed provided to said cracking furnace;

establishing a sixth signal which is representative of the number of units of said feed which are being provided to said cracking furnace per unit time;

multiplying said fifth signal and said sixth signal to establish a seventh signal which is representative of the heat which must be provided to said cracking furnace per unit time;

establishing an eighth signal representative of the heat which can be provided per unit of said fuel;

dividing said seventh signal by said eighth signal to establish a ninth signal which is representative of the units of said fuel which must be provided to said cracking furnace per unit time;

establishing a tenth signal which is representative of the actual number of units of said fuel which are being provided to said cracking furnace per unit time;

comparing said ninth signal and said tenth signal and establishing an eleventh signal responsive to the difference between said ninth signal and said tenth signal; and manipulating the flow of fuel to said cracking furnace in response to said eleventh signal.

5. A method for controlling a cracking furnace in which a feed stream is cracked to produce a gaseous mixture, wherein the crackable components of said feed stream consist essentially of ethane and propane, wherein ethane is the principal component of said feed stream, and wherein said gaseous mixture contains ethane, propane, ethylene and propylene, said method comprising the steps of:
   (a) analyzing said feed stream to determine the concentration (X2) of ethane in said feed stream;
   (b) analyzing said feed stream to determine the concentration (X3( of propane in said feed stream;
   (c) analyzing said gaseous mixture to determine the concentration (Z2) of ethane in said gaseous mixture;
   (d) estimating the conversion (Y2) of ethane in said cracking furnace;
   (e) calculating the conversion (Y3) of propane in said cracking furnace based on the value of Y2 and simultaneous conversion data;
   (f) calculating the expansion of ethane in said cracking furnace based on the value of Y2 and expansion versus conversion data;
   (g) calculating the expansion (A3) of propane in said cracking furnace based on the value of Y3 and expansion versus conversion data;
   (h) calculating the expansion (A) of said feed stream in said cracking furnace based on the value of X2, X3, A2 and A3;
   (i) calculating a conversion (Y2E) of ethane in said cracking furnace based on the value of A, Z2 and X2;
   (j) calculating a new estimated conversion of ethane in said cracking furnace based on the value of Y2 and Y2E and establishing a first signal representative of the new estimated conversion;

(k) establishing a second signal representative of the desired conversion for ethane;

(l) comparing said first signal and said second signal and establishing a third signal which is responsive to the difference between said first signal and said second signal; and (m) manipulating the heat supplied to said cracking furnace in response to said third signal to thereby maintain said first signal substantially equal to said second signal.

6. A method in accordance with claim 5 additionally comprising the step of repeating steps e–j at least four times, using the new estimated conversion derived in step j each time in step e, to establish said first signal.

7. A method in accordance with claim 5 wherein a fuel is supplied to said cracking furnace with the combustion of said fuel supplying heat to said cracking furnace, wherein said third signal is scaled so as to be representative of the temperature of said gaseous mixture required to maintain said first signal substantially equal to said second signal and wherein said step of manipulating the heat provided to said cracking furnace in response to said third signal comprises:

establishing a fourth signal which is representative of the actual temperature of said gasous mixture;

comparing said third signal and said fourth signal and establishing a fifth signal which is responsive to the difference between said third signal and said fourth signal, wherein said fifth signal is scaled so as to be respresentative of the heat which must be provided to said cracking furnace per unit of said feed provided to said cracking furnace;

establishing a sixth signal which is representative of the number of units of said feed which are being provided to said cracking furnace per unit time;

multiplying said fifth signal and said sixth signal to establish a seventh signal which is representative of the heat which must be provided to said cracking furnace per unit time;

establishing an eighth signal representative of the heat which can be provided per unit of said fuel;

dividing said seventh signal by said eight signal to establish a ninth signal which is representative of the units of said fuel which must be provided to said cracking furnace per unit time;

establishing a tenth signal which is representative of the actual number of units of said fuel which are being provided to said cracking furnace per unit time;

comparing said ninth signal and said tenth signal and establishing an eleventh signal responsive to the difference between said ninth signal and said tenth signal; and manipulating the flow of fuel to said cracking furnace in response to said eleventh signal.

8. Apparatus comprising:

a cracking furnace means;

means for supplying a feed stream to said cracking furnace means;

means for removing a gaseous mixture, containing the cracked and uncracked components of said feed stream, from said cracking furnace means;

means for analyzing said feed stream and for establishing a first signal representative of the concentration of a first component in said feed stream;

means for analyzing said gaseous mixture and for establishing a second signal representative of the concentration of said first component in said gaseous mixture:

means for establishing a third signal which is representative of the conversion of said first component in said cracking furnace means based on the value of said first signal, the value of said second signal, an estimate of the conversion of said first component in said cracking furnace means, and a calculation of the expansion of said feed stream in said cracking furnace means;

means for establishing a fourth signal representative of the desired conversion of said first component;

means for comparing said third signal and said fourth signal and for establishing a fifth signal which is responsive to the difference between said third signal and said fourth signal; and means for manipulating the heat supplied to said cracking furnace means in response to said fifth signal to thereby maintain said third signal substantially equal to said fourth signal.

9. Apparatus in accordance with claim 8 wherein a fuel is supplied to said cracking furnace means with the combustion of said fuel supplying heat to said cracking furnace means, wherein said fifth signal is scaled so as to be representative of the temperatue of said gaseous mixture required to maintain said third signal substantially equal to said fourth signal and wherein said means for manipulating the heat provided to said cracking furnace means in response to said fifth signal comprises:

means for establishing a sixth signal which is representative of the actual temperature of said gaseous mixture;

means for comparing said fifth signal and said sixth signal and for establishing a seventh signal which is responsive to the difference between said fifth signal and said sixth signal, wherein said seventh signal is scaled so as to be representative of the heat which must be provided to said cracking furnace means per unit of said feed provided to said cracking furnace means;

means for establishing an eighth signal which is representative of the number of units of said feed which are being provided to said cracking furnace means per unit time;

means for multiplying said seventh signal and said eight signal to establish a ninth signal which is representative of the heat which must be provided to said cracking furnace means per unit time;

means for establishing a tenth signal representative of the heat which can be provided per unit of said fuel;

means for dividing said ninth signal by said tenth signal to establish an eleventh signal which is representative of the units of said fuel which must be provided to said cracking furnace means per unit time;

means for establishing a twelfth signal which is representative of the actual number of units of said fuel which are being provided to said cracking furnace means per unit time;

means for comparing said eleventh signal and said twelfth signal and for establishing a thirteenth signal responsive to the difference between said eleventh signal and said twelfth signal; and means for manipulating the flow of fuel to said cracking furnace means in response to said thirteenth signal.

10. Apparatus comprising:

a cracking furnace means;

means for supplying a feed stream to said cracking furnace means, wherein the crackable components of said feed stream consist essentially of ethane and propane and wherein ethane is the principal component of said feed stream;

means for removing a gaseous mixture, containing ethane, propane, ethylene and propylene, from said cracking furnace means;

means for analyzing said feed stream and for establishing a first signal representative of the concentration of ethane in said feed stream and a second signal representative of the concentration of propane in said feed stream;

means for analyzing said gaseous mixture and for establishing a third signal representative of the concentration of ethane in said gaseous mixture;

means for establishing a fourth signal which is representative of the conversion of ethane in said cracking furnace means based on the value of said first signal, the value of said second signal, the value of said third signal, an estimate of the conversion of ethane in said cracking furnace means, and a calculation of the expansion of said feed stream in said cracking furnace means;

means for establishing a fifth signal representative of the desired conversion of ethane;

means for comparing said fourth signal and said fifth signal and for establishing a sixth signal which is responsive to the difference between said fourth signal and said fifth signal; and means for manipulating the heat supplied to said cracking furnace means in response to said sixth signal to thereby maintain said fourth signal substantially equal to said fifth signal.

11. Apparatus in accordance with claim 10 wherein a fuel is supplied to said cracking furnace means with the combusion of said fuel supplying heat to said cracking furnace means, wherein said sixth signal is scaled so as to be representative of the temperature of said gaseous mixture required to maintain said fourth signal substantially equal to said fifth signal and wherein said means for manipulating the heat provided to said cracking furnace means in response to said sixth signal comprises:

means for establishing a seventh signal which is representative of the actual temperature of said gaseous mixture;

means for comparing said sixth signal and said seventh signal and for establishing an eighth signal which is responsive to the difference between said sixth signal and said seventh signal, wherein said eight signal is scaled so as to be representative of the heat which must be provided to said cracking furnace means per unit of said feed provided to said cracking furnace means;

means for establishing a ninth signal which is representative of the number of units of said feed which are being provided to said cracking furnace means per unit time;

means for multiplying said eighth signal and said ninth signal to establish a tenth signal which is representative of the heat which must be provided to said cracking furnace means per unit time;

means for establishing an eleventh signal representative of the heat which can be provided per unit of said fuel;

means for dividing said tenth signal by said eleventh signal to establish a twelfth signal which is representative of the units of said fuel which must be provided to said cracking furnace means per unit time;

means for establishing a thirteenth signal which is representative of the actual number of units of said fuel which are being provided to said cracking furnace means per unit time;

means for comparing said twelfth signal and said thirteenth signal and for establishing a fourteenth signal responsive to the difference between said twelfth signal and said thirteenth signal; and means for manipulating the flow of fuel to said cracking furnace means in response to said fourteenth signal.

* * * * *